US00PP09404P

United States Patent [19]

Davidson

[11] Patent Number: Plant 9,404

[45] Date of Patent: Dec. 19, 1995

[54] HYBRID TEA ROSE PLANT NAMED 'HADROMEO'

[76] Inventor: Harvey D. Davidson, #3 El Verano Rd., Orinda, Calif. 94563

[21] Appl. No.: 382,859

[22] Filed: Feb. 3, 1995

[51] Int. Cl.[6] ..... A01H 5/00

[52] U.S. Cl. ..... Plt./21

[58] Field of Search ..... Plt./20, 21, 11

*Primary Examiner*—Howard J. Locker

[57] ABSTRACT

A new rose cultivar of the Hybrid Tea Class Characterized by having medium sized dark red, loosely shaped, flat, intensely fragrant flowers on a vigorous upright bush. This plant has been designated as 'Hardromeo'. It will be marketed in the USA under the tradename of 'Olde Romeo'.

1 Drawing Sheet

The present invention relates to a new and distinctive cultivar of rose plant of the Hybrid Tea class, which was originated by my crossing 'Smooth Sailing' (not patented) as the seed parent with the pollen parent (((Old Smoothie×(Polly×Peace))×simon Bolivar))).

Among the novel characteristics possessed by the new cultivar which distinguish it from:

(a) All other cultivars of which I am aware are:

(1) A dark red flower with shadings of magenta on petal outside.

(2) Old rose form being flat, irregular and loose.

(3) Very intense old rose fragrance.

(4) Disease resistant and vigorous.

(b)

*Seed parent.*—High centered cream flowers.

*Pollen parent.*—Small dark red flower with 10 petals.

Asexual reproduction of the new rose cultivar by budding, as performed at Tulare, Calif. shows that the aforementioned and all other distinctive characteristics come true to form and are established and transmitted through succeeding propagations.

The accompanying drawing shows typical specimens of the vegetative growth and flowers of the new cultivar in different stages of developement and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers in the aforementioned color chart, e.g. "53A" is plate "53A" of The Royal Horticultural Society Colour Chart.

Parentage:

*Seed parent.*—'Smooth Sailing' (not patented).

*Pollen parent.*—(((Old Smoothie×(Polly×Peace))×Simon Bolivar))). Class: Hybrid Tea.

The following observations are made of specimens grown outdoors in Contra Costa County, Calif., in the month of September.

FLOWER

BLOOMING HABIT

A. Bud:

(1) *Size.*—Sepals enclosed, 24–26 mm from base of sepals to top of bud.

(2) *Form.*—Ovoid.

(3) *Sepals.*—34 to 38 mm in length; 8 to 10 mm extension beyond bud; no serration shown on sepal edges. Generally 3 out of 5 sepals show appendages on each side, 3 to 6 mm length. Appendages show glandular developement on edges. Sepals have fine cotton matting on inner surface, smooth on outer surface. Outside color—146C; inside—195A.

(4) *Peduncle.*—Length—95 to 105 mm; Surface—smooth, no prickles, a few glandular hairs. Strength—Firm. Color —146B, shaded 172B.

(5) *Receptacle.*—Shape—rounded, 12–14 mm. Color—146C, slight 180D.

(6) *Color.*—When sepals first divide, outside petals near to 185B.

B. Bloom:

(1) *Size.*—When open—9 to 10 cm.

(2) *Borne.*—1 to stem.

(3) *Form.*—Globular, opening flat, irregular, loose.

(4) *Petalage.*—Average number—38 to 40.

(5 ) *Color.*—Early open near to 46A with areas close to black; reverse near to 185B. Aging with increasing shades of 185B and C.

C. Petals:

(1) *Texture.*—Very firm.

(2) *Appearance.*—Flexed; satiny.

(3) *Form.*—Ruffled.

(4) *Arrangement.*—Loose and irregular.

(5) *Petaloids in center.*—Average 5 to 6.

(6) *Persistence.*—Drop off cleanly.

(7) *Fragrance.*—Very intense old rose.

(8) *Lasting quality.*—On plant 6–7 days; cut 5–6 days.

REPRODUCTIVE ORGANS

A. Stamen:

(1) *Arrangement.*—Regularly arranged around styles.

(2) *Number.*—Average 110–120.

(3) *Length.*—Average—8 to 10 mm.

(4) *Filaments.*—Color — close to 67D.

(5) *Anthers.*—Color — 23A.

(6) *Pollen.*—23C.

B. Pistil:

(1) *Styles.*—Length: 6–10 mm exposed; number: 95 to 100; color: near to 155B; heavily coated with white hairs.

(2) *Stigma.*—Color — close to 47B.

(3) *Ovary.*—Shape — oblong; 8–9 mm through center cross-section.

C. Hips: Does not set seed.

PLANT

A. Form: upright.

B. Growth: Very vigorous.

*Height.*—Average 1.5 m.

C. Stem length:

*Basal break to flower bud tip.*—Average—1 m.

D. Foliage: Compound of 3 to 5 leaflets on bloom stem; 5 7leaflets on main canes.

(1) *Mature size.*—5 leaflet — tip of leaflet to stipule base 13 –14 cm.

(2) *Quality.*—Stems well covered.

(3) *Color.*—New foliage upper side close to 139C; under side 139D. Old foliage upper side 137A, under side 137C.

(4) *Shape.*—Oval with center pointed.

(5) *Texture.*—Firm, leathery, slightly glossy.

(6) *Edge.*—Slight serration on outer edge. Average 5 points per 1 cm, with up to 1 mm peak.

(7) *Raches.*—Glandular hair on upper side; lower side: 6 to 8 hooked princkles ½–1 mm length, spaced near to ¾ to 1 cm apart.

(8) *Stipules.*—Length 13–15 mm; auricle to 5 mm. Edge of stipule to tip of auricle with many glandular hairs.

E. Resistance to disease: Mildew, rust, blackspot: very good.

F. Wood:

*New wood.*—Color close to 137B and C. Bark — smooth.

*Old Wood.*—Color close to 146A, shadings of 183B. Bark — smooth.

G. Thorns on mature wood:

*Size.*—4–8 mm

*Number per* 10 *mm.*—Primary wood 5–6 thorns; Secondary wood 20–25.

*Shape.*—Straight, downward point.

*Color.*—Close to 183A.

H. Winter hardiness: Very good.

I claim:

1. A new and distinct rose cultivar of the Hybrid Tea class, substantially as herein shown and described.

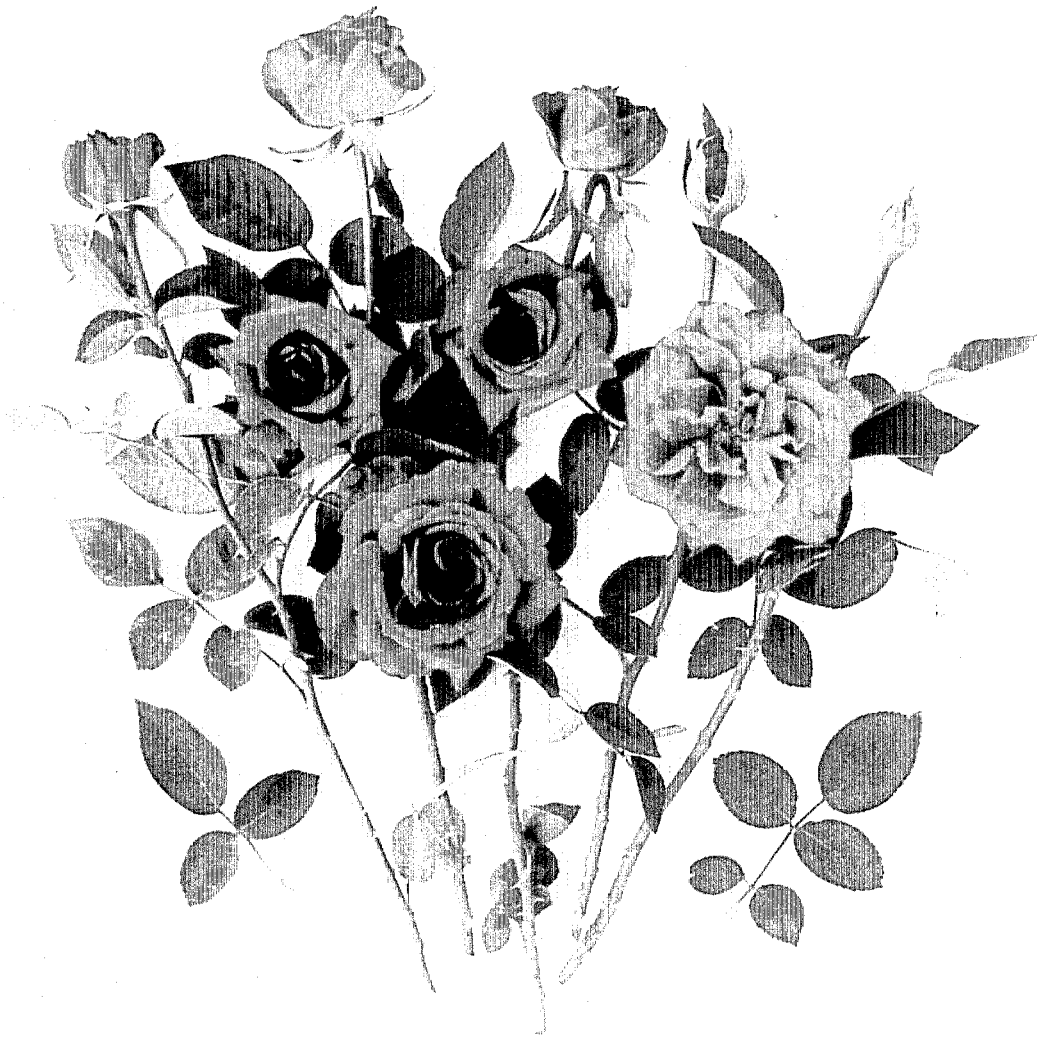

* * * * *